United States Patent [19]

Panoz

[11] Patent Number: 4,592,753
[45] Date of Patent: Jun. 3, 1986

[54] DRUG DELIVERY DEVICE

[75] Inventor: Donald E. Panoz, Southampton, Bermuda

[73] Assignee: Elan Corporation P.L.C., Athlone, Ireland

[21] Appl. No.: 555,577

[22] Filed: Nov. 28, 1983

[30] Foreign Application Priority Data

Dec. 13, 1982 [IE] Ireland ............................... 2962/82

[51] Int. Cl.$^4$ ............................................. A61M 7/00
[52] U.S. Cl. ................................................. 604/897
[58] Field of Search ............... 604/304, 308, 312, 311, 604/132, 133, 134, 135, 137, 228, 214, 890, 891, 896, 897

[56] References Cited

U.S. PATENT DOCUMENTS

| 3,964,482 | 6/1976 | Gerstel et al. | 604/896 |
| 3,968,201 | 7/1976 | Ryde et al. | 604/894 |
| 3,996,934 | 12/1976 | Zaffaroni | 604/897 |
| 4,077,407 | 3/1978 | Theeuwes et al. | 604/896 |
| 4,297,195 | 11/1981 | Golub | 128/156 |
| 4,307,717 | 12/1981 | Hymes et al. | 128/156 |
| 4,331,728 | 5/1982 | Theeuwes | 428/215 |
| 4,377,159 | 3/1983 | Hansen | 128/155 |
| 4,399,816 | 8/1983 | Spangler | 128/154 |
| 4,457,752 | 7/1984 | Vadasz | 604/135 |
| 4,460,372 | 7/1984 | Campbell et al. | 604/897 |
| 4,462,116 | 7/1984 | Sanzone et al. | 2/170 |

FOREIGN PATENT DOCUMENTS

| 0040861 | 12/1981 | European Pat. Off. . |
| 366349 | 5/1906 | France . |
| 2045593 | 3/1971 | France . |
| 1408925 | 10/1975 | United Kingdom . |
| 1519149 | 7/1978 | United Kingdom . |
| 336741 | 10/1980 | United Kingdom . |
| 2095108 | 9/1982 | United Kingdom . |

Primary Examiner—C. Fred Rosenbaum
Assistant Examiner—Sherri E. Vinyard
Attorney, Agent, or Firm—Robert Hardy Falk; Randall C. Brown

[57] ABSTRACT

A device for transdermal administration of a drug comprises a reservoir containing the drug and a supporting strap, or band, which substantially surrounds a limb of the patient and holds the reservoir in position on a limb of the patient. The reservoir is generally non permeable to the drug, but has a membrane, or plate, of defined surface area through which said drug can pass. In use, this membrane or plate is held against the patient's skin to allow the drug to be absorbed. The device further includes cooperating locking mechanisms for detachably securing the reservoir on the strap or band whereby the supply of drug can be replenished by removing the spent reservoir and inserting a fresh one containing a new supply of the drug.

6 Claims, 9 Drawing Figures

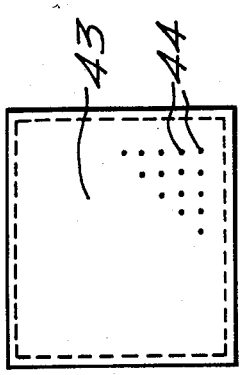
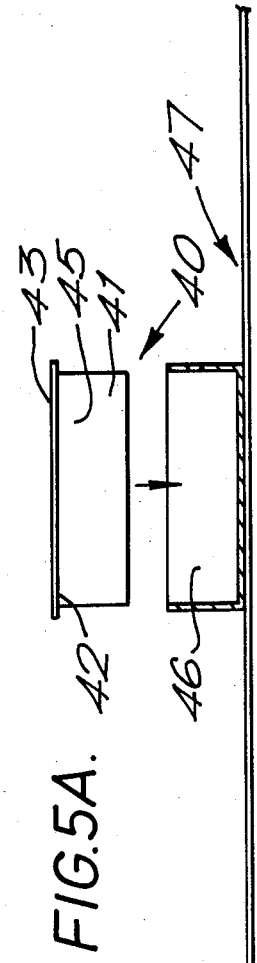
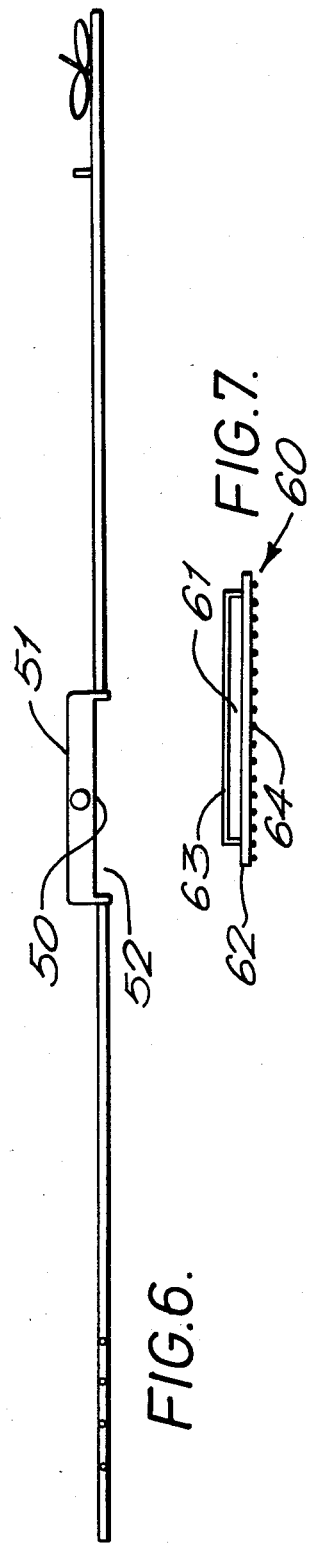
FIG.5B.
FIG.5A.
FIG.6.
FIG.7.

DRUG DELIVERY DEVICE

BACKGROUND OF THE INVENTION

1. Field of the Invention

This invention relates to a sustained release drug delivery device and, in particular, to a device for the transdermal or percutaneous delivery of drugs. The invention relates especially to a device for the systemic delivery of drugs by the transdermal route.

2. Description of the Prior Art

The advantages of administering certain drugs by the transdermal route are well known and include avoidance of drug deactivation by digestive enzymes or first-pass hepatic metabolism. However, these advantages are also characteristic of drug administration by parenteral routes such as by intramuscular injection or i.v. infusions.

Until relatively recently—circa 1980—only parenteral administration offered precise control over rate of drug entry into the bloodstream and then only when closely monitored.

A number of transdermal devices have now been developed and consist essentially of transdermal or skin patches. Certain of these transdermal devices include a rate-controlling membrane between a drug reservoir and the skin surface. The rate-controlling membrane limits the amount of drug delivered per unit area of skin surface in a manner such that the device and not the skin is dominant in controlling the rate of drug input to the skin surface and hence to the systemic circulation.

One of the first rate-controlled transdermal products was a transdermal form of scopolamine indicated for the prevention of nausea and vomiting induced by motion and known as the transdermal therapeutic system—scopolamine (TTS-scopolamine). This product, which is manufactured by Alza Corporation, California, U.S.A., is described in a paper by Shaw, J. and Urquhart J. entitled "Programmed, systemic drug delivery by the transdermal route" TIPS—April 1980, at page 208. TTS-scopolamine is also the subject of a paper by Price et al. in Clinical Therapeutics Vol. 2 No. 4, 1979.

The TTS-scopolamine system functions by permitting the drug which is highly concentrated in a small reservoir, to diffuse through a dense or microporous rate-controlling membrane. The driving force of this system, the concentration gradient of drug across the membrane, is established by the difference between the concentration of drug in the reservoir and that outside the membrane. The rate of drug release is determined by the properties of the membrane and the difference in drug concentration across the membrane.

A number of transdermal nitroglycerin patches are now on the U.S. market and are indicated for the prevention and treatment of angina pectoris due to coronary artery diseases. Although there are differences in composition, mechanism of drug delivery and appearance among the currently available transdermal nitroglycerin devices all appear to be functionally similar.

Only Ciba Pharmaceutical Company markets a transdermal nitroglycerin-patch with a rate-controlling outer membrane. An equivalent product manufactured by Key Pharmaceuticals, Inc. and sold under the trademark NITRO-DUR includes a diffusion matrix wherein nitroglycerin molecules are in equilibrium between lactose crystals and a liquid phase. When the matrix is applied to the skin, nitroglycerin molecules migrate by diffusion to the skin providing a constant flow of drug into the systemic circulation (c.f. American Pharmacy Vol. NS22 No. 2, February 1982/85).

All the currently available transdermal devices are secured to the skin by a layer of adhesive. In the case of the abovementioned transdermal nitroglycerin patches it is recommended that the patches be applied to a hairless region of the body such as the upper arm or chest. Shaving of a suitable area for application of the patch may be necessary. However, shaving may cause local skin irritation and change the permeability characteristics of the products. All the currently available transdermal products are approved for once-daily administration and it is recommended that one alternates application sites daily.

It will be appreciated that the repeated application and removal of such patches, involving a securing layer of adhesive, can result in skin irritation and sensitization with prolonged use. It will also be appreciated that a certain amount of pain and discomfort is experienced on removing the patches.

Literature supplied with the currently available transdermal devices indicates that patients may bathe or shower while wearing the products. However, a transdermal device which could be readily removed when bathing or showering would be considerably more desirable.

It is an object of the present invention to provide a transdermal device which overcomes the aforementioned disadvantages of known transdermal devices and which is convenient to use, readily removable while performing functions such as bathing or showering, cosmetically acceptable and provides the user with a degree of privacy.

SUMMARY OF THE INVENTION

Accordingly, the invention provides a device for the transdermal administration of a drug to a patient, said device comprising a reservoir for the drug to be administered, said drug being associated in the reservoir with a pharmaceutically compatible ointment, cream or jelly-like carrier, said reservoir being largely impermeable to the drug and having a defined passage means through which the drug is supplied to the skin, said defined passage means comprising a drug permeable wall member, providing a face of the reservoir, said drug permeable wall member having a first surface forming part of the reservoir and a second, opposite, surface of a defined area for contacting the skin whereby the device positively conveys the drug in the direction of the skin at a predetermined rate, means for removably attaching the reservoir to a support member, said support member being engageable with a face of the reservoir remote from that face formed by said wall member, wherein the face of the reservoir remote from that face formed by said wall member comprises a plate movable in piston-like fashion towards said wall member, the device further including a spring acting against said movable plate to cause a constant egress of ointment, cream or jelly-like carrier from the reservoir to the skin through said wall member, said support member in use substantially surrounding and being readily detachable from that portion of the patient's body to which the device is applied.

As used herein "skin contacting surface" in relation to the reservoir means either that surface of the reservoir in direct contact with the skin if such is present or, alternatively, that surface of the reservoir from which the drug leaves the reservoir during transdermal administration of said drug.

The device according to the invention is suitable for the administration of any drug which when applied to an area of intact skin acceptable to physician and patient can elicit an adequate systemic therapeutic effect. The device according to the invention has general applicability for achieving a constant therapeutic effect with any drug that is permeable to the skin and which experiences a high degree of liver metabolism. The device is particularly applicable to potent drugs with narrow therapeutic indices, short half-lives or gastrointestinal problems.

According to one embodiment of the invention the reservoir comprises a receptacle for the drug having an associated drug transfer membrane or plate through which the drug migrates to the skin surface in use, said membrane or plate having a plurality of micropores therethrough. Alternatively, the membrane or plate may be inherently drug permeable.

The drug is preferably associated in the reservoir with a pharmaceutically compatible carrier or vehicle therefor. The drug may be carried by said carrier or vehicle in its pure state or in admixture with one or more agents which facilitate its association with said carrier or vehicle or its release to the skin surface.

The drug may be carried by a suitable ointment, cream or jelly-like carrier.

One suitable form of transdermal device according to the invention is one wherein the reservoir is filled with a drug carried by an ointment or cream and the means for ensuring a supply of the drug at a predetermined rate comprises a plate movable in piston-like fashion within the reservoir by application of external pressure thereto, resulting in a constant egress of ointment from the device to the skin in use through a microporous membrane or plate comprising the skin contacting surface of the reservoir.

Preferably, the means for applying external pressure to the movable plate comprises a spring associated with the support member. The spring is most suitably a leaf spring having an end which acts against the movable plate. A coil spring may also be used or any other mechanism that exerts pressure against the movable plate such as plastics or rubber foams.

A further suitable mode of administering a drug using the device according to the invention is to incorporate the drug in a molded polymer, wax or polymer/wax block which is received within the reservoir or alternatively can be said to effectively comprise the reservoir. The polymer or wax is any suitable compatible polymer, wax or mixture thereof which can act as a carrier for and ensure a sustained release of the drug in use. Especially suitable polymers are low density polymers in which the drug can be incorporated during the molded process. Suitable waxes include beeswax, the wax sold under the trademark CASTORWAX, paraffin and carnauba waxes or, indeed, any wax conventionally used by the cosmetics industry.

Examples of polymers which can be employed, are silicone rubbers such as those sold under the trademarks DOW CORNING MDX-4-4210 clean grade elastomer and SILASTIC 382 medical grade elastomer. Collagen is also a suitable polymeric carrier support for a drug in transdermal devices according to the invention. The drug is evenly dispersed through the solid polymer and the drug molecules migrate by diffusion through the microporous membrane and hence through the skin when applied thereto.

The drug may also be loaded on to a piece of foamed plastics material or foamed rubber or, indeed, any inorganic or organic foamed polymeric material.

The device is especially suitable for the transdermal administration of effective doses of nitroglycerin, isosorbide dinitrate or isosorbide monostearate of sustained duration in the prophylactic treatment of angina. The device is also especially suitable for the transdermal administration of clonidine for the treatment of hypertension, methadone for the treatment of drug abuse and scopolamine for the treatment of motion sickness.

One suitable form of nitroglycerin transdermal device according to the invention is one wherein the reservoir is filled with an ointment or cream containing nitroglycerin at a concentration of 2% by weight such as that sold under the trademark NITRO-BID. Nitroglycerin may also be formulated as a solid polymer block as hereinbefore described, preferred polymers being collagen or silicone rubber.

Other suitable forms of nitroglycerin for use in the device according to the invention are nitroglycerin on lactose in a viscous silicone fluid or in an inorganic or organic polymer gel.

The drug permeable wall member or microporous membrane may be a rate-controlling membrane. One such rate-controlling membrane suitable for use with nitroglycerin, when the nitroglycerin in pure form diffuses from the reservoir to the skin surface, is ethylene vinyl acetate copolymer which is permeable to nitroglycerin. Another suitable nitroglycerin permeable plastics material for use as a drug transfer membrane is polyethylene.

The membrane may consist of any suitable plastics material or any inorganic or organic woven or non-woven fabric permeable to the drug being administered or any plastics material, inorganic or organic woven or non-woven fabric, or non-plastics material such as aluminum foil which has a system of evenly distributed micropores throughout its surface area which permit the transfer of a drug to the skin surface.

In the case of membranes which are non-permeable to a given drug such as sold under the trademark foil or a synthetic resin polymer, such as tetrafluoroethylene fluorocarbon polymer (TFE) or fluorinated ethylene-propylene (FEP). TEFLON aluminum in the case of nitroglycerin, micropores may be formed in the membrane by laser drilling or during the manufacture of the membrane by any suitable conventional molding technique.

The material of the membrane must, of course, be inert and be hypo-allergenic.

The reservoir itself is preferably constructed from a drug impermeable material. However, the reservoir may be comprised of a drug permeable material, in which case those parts of the reservoir through which drug migration is to be prevented, should be encased in or coated with a drug impermeable material, such as aluminum foil or a synthetic polymer in the case of nitroglycerin. The reservoir may either be integral with the support member or be a separate unit adapted for engagement with said support member.

The drug when incorporated in a block of solid polymer as discussed above may be formed with the drug transfer membrane integrally attached thereto and be adapted for reception in the reservoir proper. As stated above the block itself since it has the drug incorporated therein can be considered to effectively constitute the reservoir. However, in situ in order to prevent migration of drug in directions other than through the drug transfer membrane or plate it is necessary to encase the block in a drug impermeable receptacle in which case the block and the receptacle define the reservoir. When a drug is used in this form, the drug with the attached drug transfer membrane is ideally sold as a unit encased in a drug impermeable wrapping, such as aluminum foil in the case of nitroglycerin, thereby reducing manufacturing costs. The unit would be unwrapped prior to use and inserted in the reservoir proper, which would be a once-off purchase which could be used as long as therapy is required. Instructions would be provided with the unit to ensure that persons handling the unit would remove any drug they may have contacted. The reservoir would suitably be of high density drug impermeable plastics material, tin or aluminum in the case of a nitroglycerin transdermal device. The unit would be preferably a snap-in fit in the reservoir proper or receptacle.

Another type of unit envisaged by the present invention is a reservoir containing the drug and having the drug transfer membrane attached thereto, the reservoir being adapted for reception in a receptacle integral with the support member, the reservoir and the receptacle being provided with the respective cooperating components of a suitable locking mechanism.

The receptacle could be suitably made of aluminum, stainless steel or a suitable plastics material with a drug impermeable lining, if necessary. Alternatively, the unit could be supplied with a layer of adhesive on its face remote from the drug transfer membrane for direct attachment to the support member.

The drug transfer membrane may have incorporated therein a pre-determined quantity of a suitable embrocation or rubefacient such as camphor or menthol or other proprietary embrocation. The embrocation will cause peripheral vasodilation and hence increased skin blood flow resulting in greater drug absorption.

The use of an embrocation would be advantageous in the case of nitroglycerin. The device according to the invention will be applied to a limb, especially to the ankle, wrist, forearm or upper arm, because the support member must substantially surround that portion of the body to which the device is applied.

Studies have shown that the most efficient transdermal absorption of nitroglycerin occurs through the forehead. However, absorption through the forehead also results in the highest incidence of side effects such as headache and burning at the application site (c.f. Hansen et al Heart & Lung July-August 1979 Vol. 8 No. 4 at page 716).

The favored application site consistent with good absorption and minimal side effects is the chest. However, further studies on the percutaneous absorption of nitroglycerin in rhesus monkeys by Noonan and Webster have shown that absorption through the chest, arm and thigh for equivalent doses applied to 2-$cm^2$ areas did not result in statistically different absorption values (Journal of Pharmaceutical Sciences Vol. 69 No. 3, March 1980).

To improve initial absorption through the limbs using the device according to the invention one preferably includes a suitable embrocation in the drug transfer membrane.

The device is preferably secured to the site of application by a fastening mechanism integral with the support member. The support member preferably includes a pair of straps and the fastening mechanism may be a conventional buckle mechanism or more especially a system of cooperating synthetic material parts which adheres when pressed together, such as that sold under the trademark VELCRO.

However, it is not necessary that the device completely surrounds the site of application. As long as the device substantially surrounds and ensures permanent contact between the drug transfer membrane and the skin during use and the maintenance of therapeutic blood levels of the drug the objects of the invention will be met. Accordingly, the support member can take the form of a band suitably modified as necessary to support the drug-carrying reservoir or receptacle which can be constrained to ensure a tight and permanent fit to the site of application. Alternatively, the support member can take the form of an elasticized band. Such bands fall within the scope of the invention since they would be readily removable from the site of application as required by the wearer. The support member suitably takes the form of an elasticized wrist band such as a sweat band worn by tennis players and squash players. The band is also suitably insulated so as to maintain body temperature.

It will be appreciated that a patient may concurrently wear more than one device according to the invention to achieve an adequate or desired therapeutic effect. For example, the patient could wear one device on each wrist.

The support member may also suitably take the form of a watch or bracelet which will serve to camouflage and divert attention from or, indeed, hide the device. The watch or bracelet may be provided on its rear face with a hollow portion, or, alternatively, a socket defined by an upstanding peripheral wall, constituting a receptacle for the drug reservoir. The reservoir may also be stuck directly to the rear face of the watch by a layer of adhesive as described above.

The reservoir may be of any suitable shape but will usually be circular, square or rectangular depending on the choice of support member.

A suitable surface area for the drug transfer membrane will be a surface area in the region of 9-25$cm^2$.

However, it will be appreciated that the surface area of the drug transfer membrane will be determined by a number of factors such as severity of condition and required therapeutic effect and also by factors such as appearance.

Conventional transdermal devices or skin patches are recommended by once-daily application. It will be appreciated that the device according to the invention is readily adaptable for a longer duration of use and that the duration of use may be as long as one week.

An additional suitable device for the transdermal administration of a drug to a patient according to the invention is one which includes a reservoir for the drug wherein the reservoir includes side walls, a skin-contacting wall and a bottom wall. The side and bottom walls of the reservoir are drug impermeable and the bottom wall is movable towards the skin-contacting wall. The skin-contacting wall has a passage means through which the drug can pass. The device also includes a support member in the form of a fastenable strap and locking means for detachably mounting the reservoir on the support member. Spring means are mounted on the support member and apply force to the movable wall to move it in the direction of the skin-contacting wall to cause the drug to be dispensed through the skin-contacting wall. The skin-contacting wall preferably is a microporous plate of aluminum foil. The drug preferably is an ointment containing 2% nitroglycerin. The spring means preferably is a leaf spring.

The present invention is also directed to a method of administering a drug transdermally to a patient, which comprises applying a device as described above to the desired site of drug administration.

DESCRIPTION OF THE DRAWINGS

The invention will be understood from the following description of embodiments thereof given by way of example only with reference to the accompanying drawings in which:

FIG. 5A is an exploded front elevation of a third embodiment of a device according to the invention;

FIG. 5B is a plan view of a drug transfer membrane forming part of the device shown in FIG. 5A;

FIG. 6 is a schematic representation of a watch modified to form a support member for a device according to the invention; and FIG. 7 is a front elevation of a further embodiment of a device according to the invention suitable for direct attachment to the rear face of a watch.

DETAILED DESCRIPTION

Figure 1B:
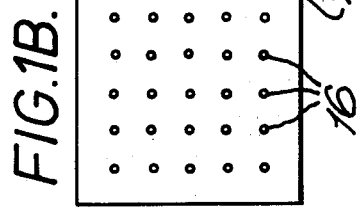
FIG. 1B is a plan view of a drug transfer membrane forming part of the device shown in FIG. 1A.
Figure 1A:
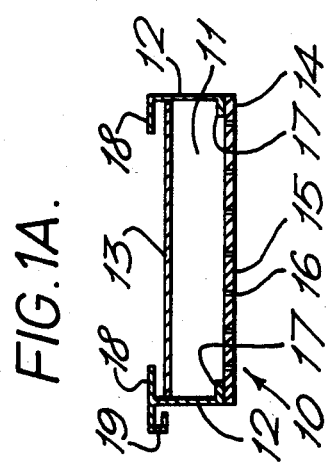
FIG. 1A is a schematic representation of a front elevation of one embodiment of a device according to the invention.
Figure 3:
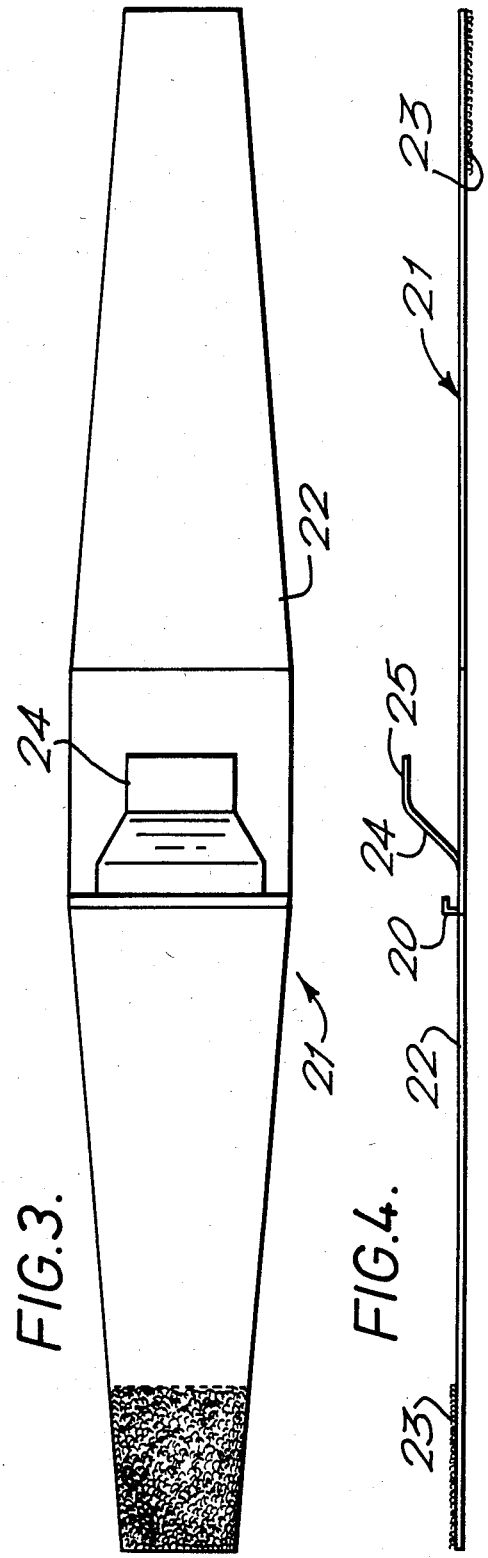
FIG. 3 is a plan view of a support member for use with the device shown in FIG. 1A.

Referring to FIG. 1A of the drawings there is illustrated a transdermal device indicated generally at 10. The device 10 comprises a reservoir 11 for a drug to be delivered transdermally, said reservoir 11 being defined by side walls 12 and a bottom wall comprising a movable plate 13 which moves on application of external pressure thereto as hereinafter described. The reservoir 11 has a skin contacting surface 14 in the form of a drug transfer microporous plate 15 constructed from aluminum foil and having micropores 16 uniformly distributed throughout its surface area. The plate 15 is affixed to a pair of shoulders 17 extending inwardly from side walls 12. The reservoir 11 is provided with a pair of stops 18 formed as inwardly projecting extensions of side walls 12 and which serve to limit the movement of the plate 13 in a direction away from the microporous plate 15. The reservoir 11 is also provided with one element 19 of a slide locking mechanism and which element 19 is interengageable with a corresponding cooperating element 20 provided on a support member indicated generally at 21. The support member 21 consists essentially of a strap 22 fastenable by means of strips 23 of synthetic material which adheres when pressed together. The support member 21 is provided intermediate its length with a leaf spring 24 having a face 25 for engagement with the plate 13 of the reservoir 11.

The reservoir 11 contains a filling quantity of ointment containing 2% nitroglycerin.

In use, the reservoir 11 is attached to the support member 21 by interengagement of the elements 19 and 20 of the slide locking mechanism. The support member 21 is then attached to the desired site of application such as the wrist of a patient (not shown). When the device 10 is in position on the wrist of the patient, the spring 24, which is suitably tensioned, causes piston-like movement of the plate 13 in a direction towards the plate 15 and progressive egress of the ointment through the micropores 16 in the plate 15 onto the skin of the patient. The spring tension and the diameter and number of micropores determines the availability of the nitroglycerin to the patient.

The device 10 can be readily removed from the wrist when it is desired to replace the reservoir by a new reservoir or, alternatively, the device can be removed temporarily when the patient desires to take a shower or bathe.

In the case of the device 10, it will be appreciated that the nitroglycerin is actively applied to the site of application due to pressure exerted by the spring 24 and the resulting movement of the plate 13 and hence the ointment.

Figure 2:
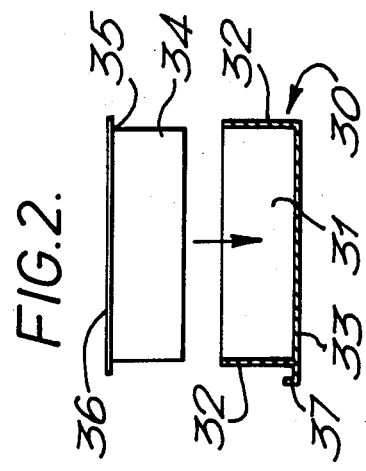
FIG. 2 is an exploded view of a portion of a second embodiment of a device according to the invention.
Figure 4:
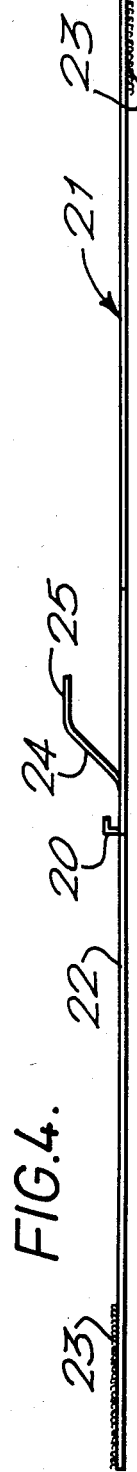
FIG. 4 is a front elevation of the support member shown in FIG. 3.

Referring to FIG. 2 of the drawings there is illustrated a second embodiment of a device according to the invention, indicated generally at 30. The device 30 comprises a reservoir 31 of tin having side walls 32 and a bottom wall 33. The reservoir receives a block of solid silicone rubber 34 having nitroglycerin substantially uniformly incorporated therein. The block of silicone rubber 34 has molded to one surface 35 thereof a rate-controlling microporous membrane 36 of ethylene vinyl acetate copolymer which is permeable to nitroglycerin and through which the nitroglycerin diffuses in use to the site of application of the device 30. The reservoir 31 is provided adjacent its bottom wall 33 with one element 37 of a locking mechanism which is interengageable with a cooperating element (not shown) provided on a support member (not shown) similar to that depicted in FIG. 4.

The source of energy for the movement of nitroglycerin through the skin and into the systemic circulation is the thermodynamic energy provided by the nitroglycerin in the reservoir 31 and by virtue of which the nitroglycerin diffuses from a zone of high concentration to a zone of lower concentration resulting in a constant release of nitroglycerin into the bloodstream.

Referring to FIG. 5A of the drawings there is illustrated a third embodiment of a device according to the invention indicated generally at 40. The device 40 consists of a molded block of collagen 41 having nitroglycerin uniformly distributed therethrough. Attached to one surface 42 of the block 41 is a skin contacting plate 43 of a synthetic resin polymer material, such as that sold under the trademark TEFLON having micropores 44 uniformly distributed over its entire surface area. The plate 42 is coated or impregnated with a layer of a suitable rubefacient such as camphor to promote skin absorption, in use, of nitroglycerin by causing peripheral dilation and increased skin blood flow.

The block 41 and the plate 42 are sold as a unit 45 which is received in a receptacle 46 forming part of a support member indicated generally at 47. The receptacle 46 is composed of aluminum which is impermeable to nitroglycerin. Prior to inserting the block 41 in the receptacle 46, an aluminum foil wrapper (not shown) is removed therefrom. Instructions are furnished with the unit 45 stating that the hands should be washed after handling of the unit so as to remove any traces of nitroglycerin adhering to the hands.

The device 40, when positioned in the receptacle 46, is applied to the site of application and secured thereto by a fastening (not shown) provided on the support member 47.

Nitroglycerin diffuses from the collagen block 41, by passive diffusion down a concentration gradient as in the case of the embodiment of the invention depicted in FIG. 2 of the drawings, through the micropores 43 on to the skin from whence it is absorbed into the systemic circulation.

It will be appreciated that the block 41 could also be a molded block of any suitable low density polymer or wax or polymer/wax mixture as hereinabove described.

Referring to FIG. 6 of the drawings there is illustrated a fourth embodiment of the present invention wherein the rear face 50 of a man's wristwatch 51 is modified to define a receptacle 52 for receiving a device of the kind depicted by reference numeral 40 in FIG. 5A of the drawings. The device would suitably be a snap-in fit in the receptacle 52 or, alternatively, provided with an adhesive layer for securing it to the receptacle 52. Furthermore, the device would have a largest dimension of 3 or 5 cm. and the type of watch with which the device could be used would be limited accordingly.

A suitable device for use with the watch 51 depicted in FIG. 6 of the drawings is a device of the type shown in FIG. 7. The device, indicated generally at 60, comprises a block of a molded polymer 61, such as the medical grade elastomer sold under the trademak SILASTIC, having nitroglycerin microsealed therein and uniformly dispersed throughout the polymer. The block of polymer 61 is encased in, and secured to, a backing plate 62 by a rate-controlling skin of polyethylene 63 material. The backing plate 62 is provided with a layer of adhesive 64 for securing the device 60 to a suitable support member such as the rear face of a watch.

The advantages of the device according to the invention will be readily apparent from the above description. In particular, devices according to the invention are convenient to use and ensure an immediate release of active ingredient to the skin, with the skin itself acting essentially as the rate-controlling factor for systemic drug administration. The devices obviate any pain or discomfort normally associated with the removal of known devices. They are also generally inexpensive to use when compared with conventional transdermal patches, since one need simply buy one support member, if a support member other than a watch is to be used, and simply replace the source of drug, which is optimally a drug reservoir and associated drug transfer membrane which are integrally formed.

A further advantage of devices according to the invention is that they may be readily designed to deliver a drug over a period of days or even one week without replacement.

I claim:

1. A device for the transdermal administration of a drug to a patient, said device comprising a reservoir for the drug to be administered, said drug being associated in the reservoir with a pharmaceutically compatible ointment, cream or jelly-like carrier, said reservoir being largely impermeable to the drug and having a defined passage means through which the drug is supplied to the skin, said defined passage means comprising a drug permeable wall member, providing a face of the reservoir, said drug permeable wall member having a first surface forming part of the reservoir and a second, opposite, surface of a defined area for contacting the skin whereby the device positively conveys the drug in the direction of the skin at a predetermined rate, means for removably attaching the reservoir to a support member, said support member being engageable with a face of the reservoir remote from that face formed by said wall member, wherein the face of the reservoir remote from that face formed by said wall member comprises a plate movable in piston-like fashion towards said wall member, the device further including a spring acting against said movable plate to cause a constant egress of ointment, cream or jelly-like carrier from the reservoir to the skin through said wall member, said support member in use substantially surrounding and being readily detachable from that portion of the patient's body to which the device is applied.

2. A device according to claim 1, wherein the spring is a leaf spring having an end which acts against the movable plate.

3. A device for the transdermal administration of a drug to a patient comprising:
   a reservoir for the drug;
   said reservoir comprising side walls, a skin-contacting wall and a bottom wall, said bottom wall being movable towards said skin-contacting wall;
   said side and bottom walls being drug impermeable;
   said skin-contacting wall having passage means through which said drug can pass;
   a support member in the form of a fastenable strap;
   locking means for detachably mounting the reservoir on the support member;
   spring means mounted on said support member and applying force to said movable wall to move it in the direction of the skin-contacting wall to cause said drug to be dispensed through said skin-contacting wall.

4. A device according to claim 3, wherein the skin-contacting wall is a microporous plate of aluminum foil.

5. A device according to claim 4, wherein the drug is an ointment containing 2% nitroglycerin.

6. A device according to claim 3, wherein the spring means is a leaf spring.

* * * * *

UNITED STATES PATENT AND TRADEMARK OFFICE
CERTIFICATE OF CORRECTION

PATENT NO. : 4,592,753

DATED : June 3, 1986

INVENTOR(S) : Donald E. Panoz

It is certified that error appears in the above-identified patent and that said Letters Patent is hereby corrected as shown below:

The title "Drug Delivery Device" should read -- Device for Transdermal Administration of a Drug--.

Column 3, line 57, the language "molded" should read --molding--.

Column 4, lines 44-47, the language "sold under the trademark foil or a synthetic resin polymer, such as tetrafluoroethylene fluorocarbon polymer (TFE) or fluorinated ethylene-propylene (FEP). TEFLON aluminum" should read --aluminum foil or a synthetic resin polymer, such as tetrafluoroethylene fluorocarbon polymer (TFE) or fluorinated ethylenepropylene (FEP) sold under the trademark TEFLON--.

Column 4, line 60, the language "synthetic polymer" should read --synthetic resin polymer--.

Column 6, line 51, the word "by" should read --for--.

Signed and Sealed this

Twentieth Day of January, 1987

*Attest:*

DONALD J. QUIGG

*Attesting Officer*  *Commissioner of Patents and Trademarks*